(12) United States Patent
Walton

(10) Patent No.: US 7,144,252 B2
(45) Date of Patent: Dec. 5, 2006

(54) DENTAL TOOL WITH SHEAR PIN HANDLE

(75) Inventor: James Walton, 1230 B 52nd St., West Palm, FL (US) 33407

(73) Assignee: James Walton, Las Vegas, NV (US)

( * ) Notice: Subject to any disclaimer, the term of this patent is extended or adjusted under 35 U.S.C. 154(b) by 0 days.

(21) Appl. No.: 10/423,799

(22) Filed: Apr. 25, 2003

(65) Prior Publication Data

US 2004/0214137 A1    Oct. 28, 2004

(51) Int. Cl.
A61C 3/00     (2006.01)
B25B 23/143   (2006.01)
A61C 8/00     (2006.01)

(52) U.S. Cl. .................. 433/141; 433/173; 81/471

(58) Field of Classification Search ........... 433/141, 433/173–174, 225; 81/467, 471–472, 481
See application file for complete search history.

(56) References Cited

U.S. PATENT DOCUMENTS

| | | | |
|---|---|---|---|
| 3,753,625 A * | 8/1973 | Fabrizio et al. | 408/239 R |
| 5,030,096 A | 7/1991 | Hurson et al. | |
| 5,295,831 A | 3/1994 | Patterson et al. | |
| 5,347,894 A | 9/1994 | Fischer | |
| 6,162,053 A | 12/2000 | Hollander | |
| 6,186,785 B1 * | 2/2001 | Rogers et al. | 433/141 |
| 6,206,696 B1 * | 3/2001 | Day | 433/141 |
| 6,308,598 B1 * | 10/2001 | O'Neil | 81/467 |

* cited by examiner

*Primary Examiner*—John J Wilson
(74) *Attorney, Agent, or Firm*—McHale & Slavin, P.A.

(57) ABSTRACT

A tool is used to limit the torque applied to tighten the threaded connection of prosthesis components placed in skeletal bones, for example dental implants. The device had a handle, a retaining screw, a single use torque limiting shear pin and a drive shaft. The handle has a tapered counter sunk cross bore with left handed threads to allow installation of a drive shaft which engages a torque limiting shear pin which, in turn, engages a left hand threaded retaining screw. The drive shaft extends from the handle to engage any threaded fastener that has a head that corresponds to the drive shaft end. The drive shaft and the shear zone of the shear pin are completely isolated within the wrench handle so that all rotational force is utilized in the actual shearing of the shear pin to a torque accuracy of ±0.3 Ncm, approximately.

9 Claims, 3 Drawing Sheets

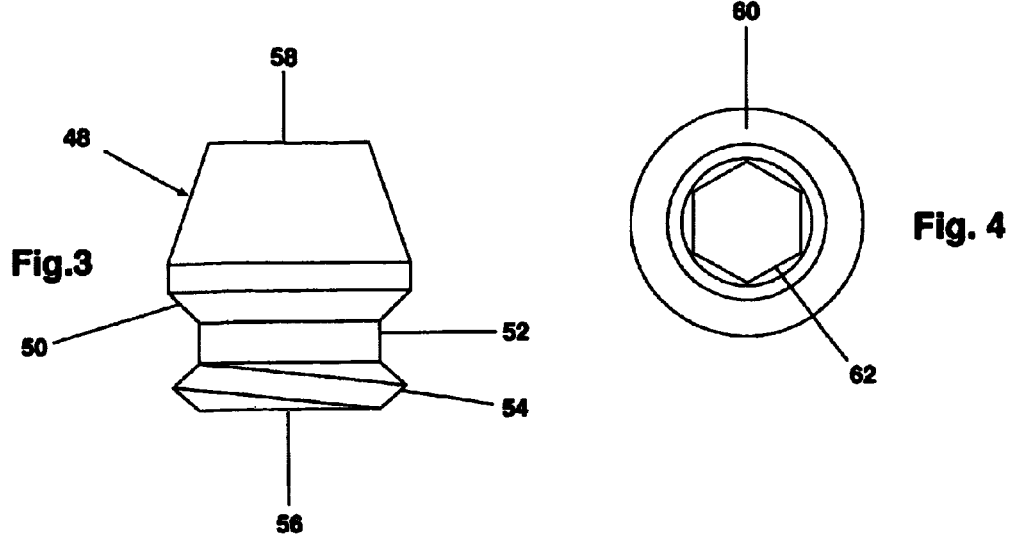
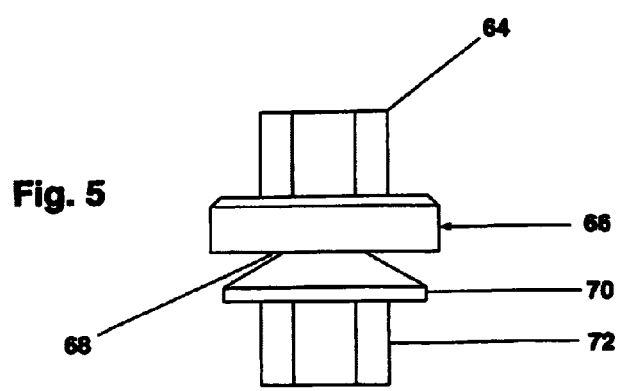

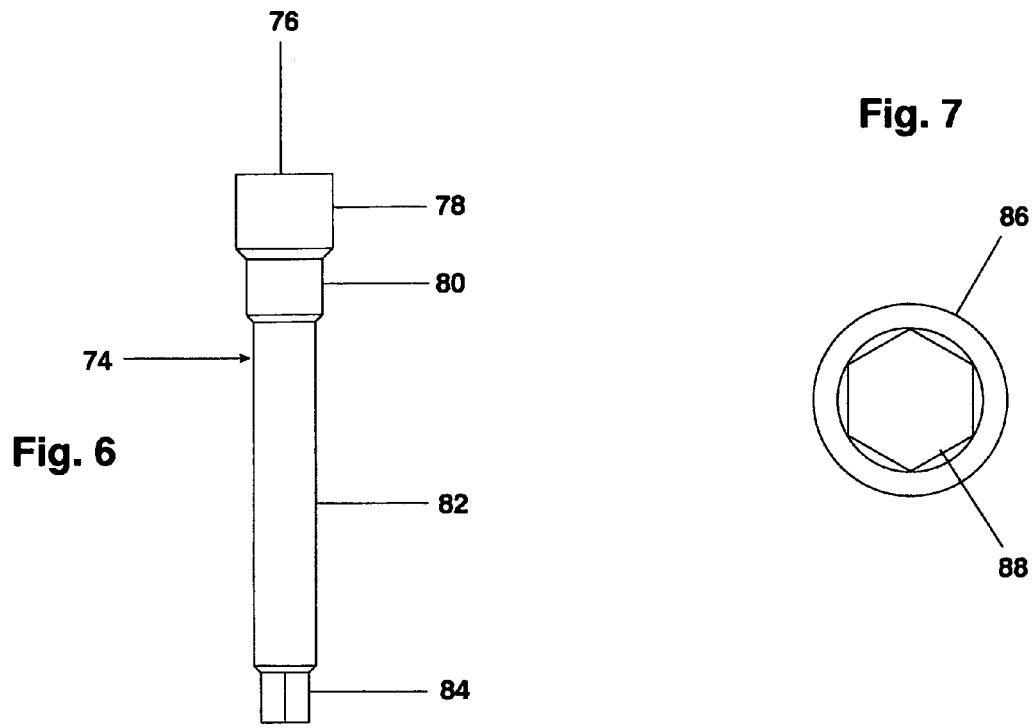
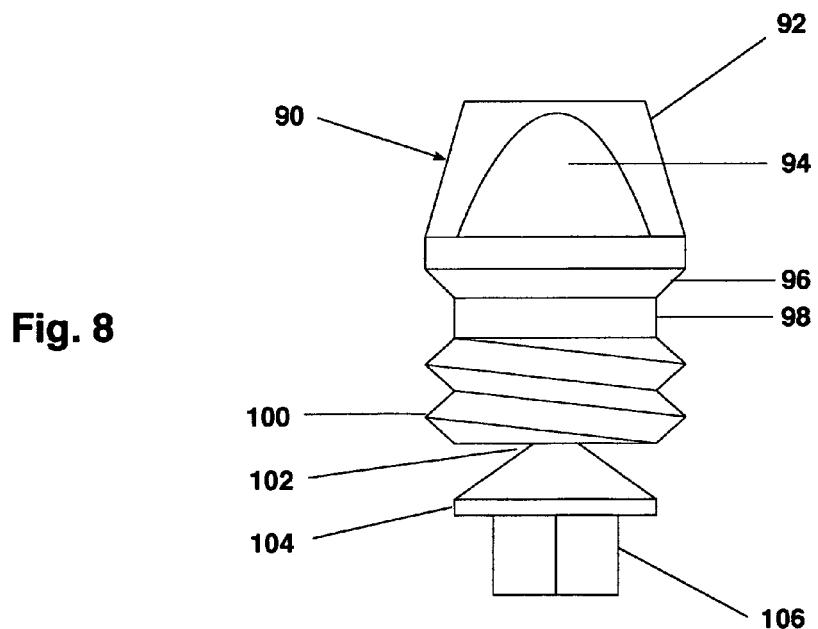

DENTAL TOOL WITH SHEAR PIN HANDLE

BACKGROUND OF THE INVENTION

This invention relates to the field of medicine, for example, dentistry, and the mounting of all types of prostheses to osseointegrated implants.

Tooth loss in humans is an unfortunate fact of life for a large portion of the population. The concomitant loss of masticatory function and esthetics is a very real problem that has only been able to be effectively addressed by various treatment modalities in modern times. Traditional restorative treatment for tooth loss has been placement of fixed partial prostheses (bridgework), removable partial prostheses (partial dentures), and complete removable prostheses (complete dentures). The main shortcoming of all of these treatment modalities is the lack of underlying bone support for the prosthetic replacement, making the stability of some prostheses tenuous at best.

Osseointegrated dental implants have vastly improved this situation by providing solid bone support for all of the types of prostheses already mentioned. Currently, most dental implants have one of two basic designs. Both designs have an implant component that is surgically placed in either the maxilla or the mandiblle.

This surgical placement leaves a portion of the implant above the bone so that an abutment may be affixed to it. The abutment protrudes from the patients gum tissue, and it is on the abutment that the prosthesis is affixed. The manner of fixation of the abutment to the implant is what separates the two main designs. In one design, the abutment has threads machined into it, and it directly screws into the implant, while the other, more popular design, has a separate retaining screw to fix the abutment to the implant. Respectively, abutments are referred to as direct threading abutments and screw retained abutments. In either case, however, both types of abutments need to be tightened to a predetermined torque which accomplishes two things: 1) Application of proper torque limits the possibility of the shearing (failure) of the retaining screw or direct threading abutment due to the over application of torque. Retrieving sheared screw threads which remain inside the implant without damaging the implant itself is a virtual impossibility due to the miniature nature of the screw threads. 2) Proper application of torque limits the possibility of abutment loosening, which requires an office visit by the patient to resolve. These office visits to simply tighten a loose abutment are time consuming, costly and annoying not only for the patient, but the dentist as well.

Traditionally, direct threading abutments and screw retained abutments have been torqued with miniature ratchet torque limiting wrenches, which are costly to manufacture, assemble and calibrate. Unfortunately, after repeated use and more importantly, after repeated autoclaving, they lose their initial accuracy. As a result, these wrenches need to be returned to the manufacturer on a periodic basis to be recalibrated and/or repaired. Additionally, to maintain even some accuracy between recalibration procedures, these wrenches need to be disassembled and lubricated before each autoclaving cycle (between each patient use). So on top of being very expensive devices to purchase initially, the level of maintenance required to maintain acceptable accuracy in conventional ratchet style torque wrenches is an additional costly and unacceptable burden placed on the dentist. The net result is that only a limited number dentists who place large numbers of implants actually own an implant torque wrench, even though the benefits of properly torquing implant abutments are abundantly clear.

To make matters worse, because the dental implant market is still rather fragmented, each manufacturer has its own retaining screw head drive design and their own recommendations for application of torque. The net result is that there is no standardization of components or torque recommendations, and the torque wrench from one manufacturer will often be useless with another manufacturer's implant system because their torque wrenches by design have no adjustability or adaptability with other implant systems. Thus, if the dentist switches implant systems, he/she usually has to purchase a brand new expensive torque wrench to be used with the new system.

Also, in orthopedic implants, generally, there are applications in which an implant is screwed directly into the skeletal bone or into an abutment placed in the bone, e.g., spinal plates and cages. These implant techniques employ torque wrenches of various designs to limit the amount of torque placed on the implant.

U.S. Pat. No. 5,030,096 to Hurson et al illustrates a conventional dental implant that requires an insertable wrench to place the device.

Hollander, U.S. Pat. No. 6,162,053, describes a straight dental wrench with a spring loaded bearing. At a particular torque load the spring compression is overcome and the wrench is disabled.

Patterson et al, U.S. Pat. No. 5,295,831, teaches a dental wrench which has a weakened portion along a shaft that may be straight or bent. The shaft will deform at the weakened portion upon reaching the designed torque.

U.S. Pat. No. 5,347,894 to Fischer discloses a wrench for inserting halo pins in the skull. The wrench has two shear points which will break at a particular amount of torque. The device is designed so that the components of the wrench remain attached after shearing apart to prevent loss of parts.

Therefore, a need exists for a new torque limiting wrench that is simple in design, that is inexpensive to manufacture and purchase, that has the flexibility to economically adapt to any implant system on the market today or in the future, that requires absolutely no maintenance whatsoever, and that delivers torque with the safety and accuracy befitting the precision torque requirements of implants.

SUMMARY OF THE PRESENT INVENTION

Disclosed is a torque wrench used to torque direct threading abutments or screw retained abutments which are affixed to dental implants or other prosthesis. The tool is comprised of a cylindrical handle with enlarged working head, through which a cross-bore is countersunk and tapped with left handed threads. The cross-bore is larger at its entrance than its exit. Within this cross-bore, a retaining screw, a shear pin and a drive shaft are engaged one to the other and are retained inside the working head of the handle by the left hand threads of the retaining screw engaging the left hand threads tapped into the cross-bore of the handle. The drive shaft protrudes from the exit of the cross-bore in the handle. The shear point of the shear pin and the entire drive shaft are devoid of contact with any portion of the handle. To use the device, the drive end of the drive shaft is engaged into the socket of a direct threading abutment or the retaining screw of a screw retained abutment. The handle is turned clockwise until the shear pin shears at the shear zone. A novel feature of the device is that the drive shaft and shear zone are isolated from any contact with the wrench handle during use. Because of this, no undesirable and unpredictable frictional forces are added to the torque necessary to shear the shear pin, and which are subsequently transferred to the abutment retaining screw, direct threading abutment or threaded fastener via the drive shaft. Additionally, the design of the shear zone on the shear pin as a circle and not a cylinder, by the machining of a knife edged groove into the shear pin forces shear at an exact diameter and cross sectional area. These features along with the shear pin's material which is best made from Alloy 360 brass all contribute to the very high accuracy of the device. Another novel feature of the invention is the use of left handed threads in the handle and the retaining screw. When the wrench is in use in a clockwise direction, the only working direction currently in use by all dental implant manufacturers, as the drive shaft transmits the resistance to turn to the shear pin and from the shear pin to the retaining screw, this actually tightens the retaining screw into the handle. This is until the shear pin shears, at which point tightening of the retaining screw ceases and the drive shaft rotates freely. Once the shear pin shears, the device may be removed from the operating field with all of the components of the wrench retained securely within the wrench handle, preventing loss of components within the operating field, as well as prevention of aspiration of any components by the patient despite the fact that the drive shaft is now separated from one half of the shear pin. A benefit of the use of the retaining screw is that various lengths of drive shafts as well as drive shafts with different shapes and sizes of drive ends, as well as a plurality of shear pins with various preset torques may be used interchangeably at any time with a single wrench, enabling the device unmatched flexibility and adaptability of use. Additionally, the use of shear pins to deliver torque eliminates all wrench maintenance and calibration. The shear pin is the actual working member of the invention. By design, since it shears upon use, it cannot be reused. Therefore, a new shear pin is needed for each use. This being the case, there is nothing to oil or maintain, and nothing to calibrate, unlike the ratchet style wrenches mentioned previously, because the spent shear pins are discarded after each use.

It is a principal object of the present invention to provide a new and improved torque limiting wrench of simple design and low cost of manufacture. A wrench that never requires any maintenance or calibration, and that has adaptability for use with any implant system. A wrench that delivers torque with an accuracy greater than any existing single use system. And a torque limiting wrench that is very safe to use.

It is another object of the present invention to provide a torque wrench that limits the ability of a direct threading implant abutment, or screw retained abutment from loosening prematurely.

It is yet another objective of the present invention to limit the chance for premature failure of direct threading abutments, or premature failure of abutment retaining screws due to overapplication of torque.

A further objective of this invention is to provide a tool that limits torque applied to threaded fasteners and to direct threading abutments and implant abutment retaining screws.

Another objective of the present invention is to provide a torque wrench that can deliver varying amounts of torque by utilization of single use shear pins that shear at predetermined levels of torque.

A still further objective of this invention is to provide a torque wrench that allows application of torque to varying screw head designs by utilization of drive shafts with varying drive ends each of which is completely interchangeable with the shear pins of this invention.

A still further objective of the present invention is to provide a dental torque wrench in which all components of the tool are retained in the tool after the shearing of the shear pin, preventing loss of any components in the surgical field and aspiration of any component by the patient.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 3 is an enlarged partial perspective view of the retaining screw of the invention;

FIG. 4 is a top view of the retaining screw of the invention;

FIG. 5 is an enlarged side perspective of the preferred embodiment of the shear pin of the invention;

FIG. 6 is an enlarged side view of the drive shaft of the invention;

FIG. 7 is an enlarged top view of the drive shaft of the invention; and

FIG. 8 is an enlarged side perspective of an alternative embodiment of the shear pin that combines the function of the shear pin and the retaining screw of the invention.

DETAILED DESCRIPTION OF THE INVENTION

Figure 1:
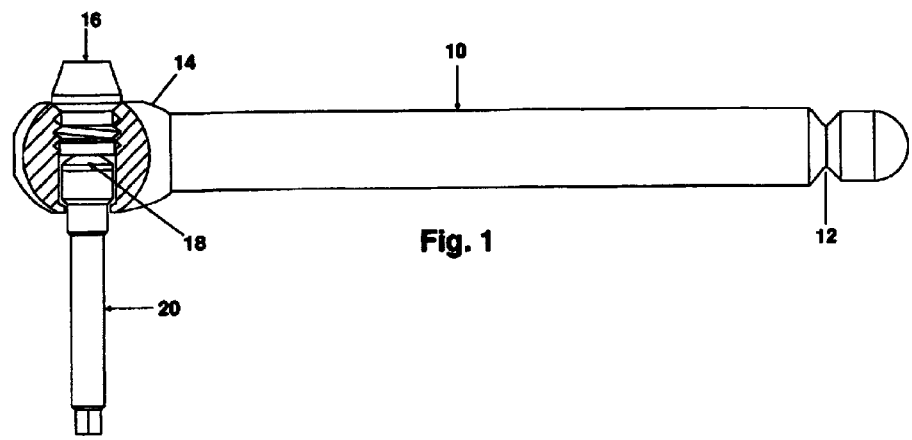
FIG. 1 is a perspective and partial section of the tool of this invention.

FIG. 1 shows a side view of the preferred embodiment of the entire invention with a cutaway showing all the components of the invention assembled and ready for use. The wrench handle 10 is generally of cylindrical shape and made of a sufficiently strong material to deliver the proper amount of torque for the application, preferably made from stainless steel or titanium. Safety groove 12 is incorporated into the wrench handle to allow dental floss to be tied around it to prevent aspiration of the entire device as the invention is rather small in overall size. Enlarged head 14 is incorporated into the wrench handle to provide sufficient material to enclose retaining screw 16, shear pin 18 and drive shaft 20.

Figure 2:
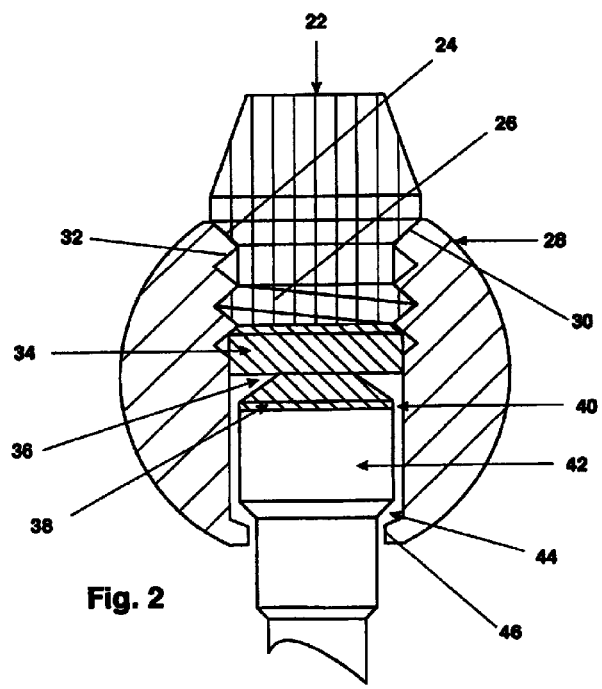
FIG. 2 is an enlarged sectional view of the tool of FIG. 1.

FIG. 2 shows an enlargement of the cutaway shown in FIG. 1. The retaining screw 22, is preferably made from stainless steel or titanium although other materials would be suitable, with a tapered head, a countersink portion 24 which seats into a corresponding countersink 30 in wrench handle 28, thus centering retaining screw 22 in wrench handle 28 and limiting its travel. Wrench handle 28 has a cross-bore with an entrance countersink 30, threaded portion 32, and an exit 46 that is smaller in diameter than the entrance of the through bore. Retaining screw threads 26 are left hand, as are the corresponding threads 32 of wrench handle 28. Retaining screw 22 has a through-bore centered along its long axis which will be shown in FIG. 4. This through-bore has a shape internally broached into it along its entire length. The cross sectional shape of the broaching is preferably hexagonal, but may be any shape other than round. The broaching serves two purposes: 1) It allows the retaining screw 22 to be inserted and removed from the wrench handle 28 with an allen wrench; 2) The internal broaching of the retaining screw also allows engagement of the retaining screw engagement means of shear pin 34. The engagement means of the shear pin will be described later and is illustrated in FIG. 5. The visible portion of the shear pin in FIG. 2 is comprised of portions 34, 36 and 38. What is not visible are engagement means for retaining screw 22 and drive shaft 42. Again, these engagement means will be illustrated in FIG. 5. Portion 34 of the shear pin is a centering means m that it has a close fit within the cross-bore of the wrench handle 28, preventing side to side movement of the shear pin. Portion 36 is a shear groove machined into the shear pin. Shear groove 36 is knife edged in shape which induces stress in the shear pin's material and enables very precise and more importantly, repeatable shearing of each shear pin at the point of the knife edge of the groove. By changing the diameter of shear groove 36, the torque delivered by the wrench will be changed. The shear pin is preferably made out of Alloy 360 brass, which produces the most consistently accurate results in terms of torque delivered. Portion 38 of the shear pin is known as the drive shaft stop. Drive shaft stop 38 of the shear pin has a substantially similar diameter as drive shaft 42, such that when the drive shaft engagement means of the shear pin (not viewable in FIG. 2), is engaged to the drive shaft 42, drive shaft stop 38 of the shear pin provides a seat or positive stop to the drive shaft. Drive shaft 42 is constructed of sufficiently strong material to accomplish its task without failure. It is made preferably out of heat treatable 440A, 440B or 440C stainless steel. Enlarged head portion of the drive shaft 42 is internally broached to match the shape of the drive shaft engagement means of the shear pin (again, not shown in FIG. 2). The diameter of the enlarged head portion of drive shaft 42 is substantially similar to the diameter of drive shaft stop 38 of the shear pin. The diameter of the enlarged head portion of the drive shaft 42 is also substantially larger than wrench handle bore exit 46. Thus, when the shear pin shears during use, the drive shaft which is now disconnected from one half of the shear pin and retaining screw, is nonetheless retained inside the wrench handle along with all the other components of the device. Both drive shaft stop 38 of the shear pin and the enlarged head portion of the drive shaft 42 are substantially smaller than the cross-bore of the wrench handle 28. This novel feature of the invention produces shear pin-wrench handle clearance 40 and drive shaft-wrench handle clearance 44. By completely isolating the drive shaft and shear zone of the shear pin from any contact with the wrench handle during use, frictional forces as they relate to the actual shearing of the shear pin are completely eliminated. This results in a substantial increase in the accuracy and repeatability of the torque delivered over other single use devices available until this time. Frictional forces as they relate to devices of this nature are completely unpredictable because of variances in diameter and concentricity of the contacting surfaces. This frictional force may or may not add as much as several newton centimeters to the final shear torque of the shear pin. By eliminating all frictional interference, accuracy, predictability and repeatability of the torque delivered is substantially improved. The present invention does exactly this. During use, when the wrench handle 28 is rotated in a clockwise direction after engagement of drive shaft 42 into the head of the implant abutment retaining screw or direct threading abutment, the clockwise rotation of the wrench handle 28 will actually tighten retaining screw 22 because of the left hand threads of the retaining screw 24 and the left hand threads of the wrench handle 32, thus ensuring capture of shear pin 34/38, drive shaft 42 and retaining screw 22 in the wrench handle after shear pin 34/38 shears preventing their loss in the operating field and/or aspiration by the patient.

FIG. 3 shows a side view of preferred embodiment of the retaining screw of the invention. It shows the tapered head of retaining screw 48, countersink portion 50, thread relief portion 52, left hand threads 54, shear pin engaging means 56 and alien wrench engaging means 58. The retaining screw 48 should be constructed of a material suitably strong to accomplish its task. It is preferably made from either stainless steel or titanium. The retaining screw is as its name implies. Its purpose is to retain the shear pin and drive shaft inside the wrench handle of the invention before, during and immediately after use. The retaining screw countersink portion 50 corresponds to the countersink machined into the cross-bore in the wrench handle. The countersink serves to center the retaining screw inside the cross-bore of the wrench handle as well as provide a stop for the retaining screw. The threads 54 in the preferred embodiment of the retaining screw 48 are left hand threads and correspond to the left hand threads tapped into the cross-bore of the wrench handle. This, of course, does not mean that threads of the retaining screw 48 as well as the wrench handle cannot be right hand. It is just that all dental implants use abutment retaining screws or direct threading abutments that have a right hand thread. Simply put, the threads on the tool's retaining screw and wrench handle must be opposite of hand to the threads on the implant abutment retaining screw or direct threaded abutment, in order for the retaining screw to actually tighten during use which is what is desired, since loosening of the invention's retaining screw during use could prove to be dangerous. The retaining screw 48 also has a through-bore which is centered along its long axis. A shape is broached into the bore along its entire length, preferably hexagonal, but any shape other than round. This broached shape is not visible in FIG. 3 but is shown in FIG. 4. The broached bore provides an allen wrench engaging means 58 which allows an allen wrench (hexagonal shaped) to be used to install and remove the retaining screw from the wrench handle. The broached bore simultaneously provides a shear pin engaging means 56, also preferably hexagonal, which enables the shear pin to engage the retaining screw. The retaining screw enables the installation of different shear pins of specific torques and drive shafts of various lengths and sizes and shapes of drive end thus enabling the invention to deliver a wide array of torques on an almost limitless number of screw head designs, enabling the invention to adapt to any implant design.

FIG. 4 is a bird's eye or top view of the preferred embodiment of the retaining screw of the invention. The tapered head of the retaining screw 60 is shown along with the hex broached through-bore 62. Again, the broached shape may be of any shape other than round, but is preferably hexagonal in shape. The broached through-bore simultaneously provides an alien wrench engaging means as well as a shear pin engaging means.

FIG. 5 shows a side view of the preferred embodiment of the shear pin of the invention. The shear pin's function is to shear at a predetermined torque, thus ensuring that proper torque is applied to the implant abutment retaining screw, direct threading abutment, or threaded fastener. The preferred material for construction of the shear pin is Alloy 360 brass, although other brass alloys are acceptable. Materials other than brass may be suitable, but Alloy 360 brass provides the most consistently accurate results. This, of course, does not limit the material that the shear pin can be made of. The preferred embodiment of the shear pin is comprised of a retaining screw engaging means 64, preferably hexagonal cross sectionally in shape, but any cross sectional shape other than round. A centering means 66 has a diameter just slightly smaller than the cross-bore of the wrench handle. It serves to center the shear pin within the cross-bore of the wrench handle and prevent side to side movement of the shear pin during use of the invention. Shear groove 68 is machined into the shear pin with a knife edge shape to induce stress in the material of the shear pin and force shear of the shear pin at that exact diameter and cross sectional area. The knife edge shape of the shear groove 68 causes the shear zone to be circular in shape versus cylindrical, and enables shear of the shear pin in a flat plane which means that the cross sectional area of the shear zone can be predictably controlled by control of the diameter of the shear groove 68. The greater the control of cross sectional area of the shear zone, the greater the accuracy of the delivery and repeatability of torque. Other prior art torque limiting devices have a cylindrical shear zone which may not shear in a flat plane, meaning loss of control of the cross sectional area of shear and thus increased inaccuracy of torque delivered. Thus, torque is easily varied and precisely controlled in the shear pin of the present invention by simply machining the shear groove 68 to a different diameter, as long as the shear groove is of a knife edge design. Drive shaft stop 70 has an outside diameter substantially the same as the outside diameter of the shear pin engaging means of the drive shaft. Drive shaft stop 70 additionally has an outside diameter (along with the outside diameter of the shear pin engaging means of the drive shaft), that is substantially smaller than the inside diameter of the cross-bore of the wrench handle. This enables the shear groove 68 and drive shaft stop 70 to be completely isolated from any contact with the wrench handle during use of the device, so that as the shear pin rotates before actually shearing (it typically rotates approximately 60 degrees before shearing), it has no frictional forces to overcome and be added to the torque delivered to the drive shaft and subsequently to the abutment retaining screw, direct threaded abutment or threaded fastener. This novel feature of the invention is the key to the tool's unprecedented accuracy and repeatability of torque delivery. Consistent torque accuracy of ±0.3 Ncm (±0.42 in. oz.) is routine with the use of this device. Drive shaft engaging means 72 corresponds in cross sectional shape to the shear pin engaging means of the drive shaft, and is preferably hexagonal in cross sectional shape, although it may be any cross sectional shape other than round. Additionally, as mentioned previously, use of the shear pins to deliver preset torque eliminates wrench maintenance and calibration.

FIG. 6 is a side view of the preferred embodiment of the drive shaft of the invention. The function of the drive shaft is to transmit the torque developed by the shearing of the shear pin to the screw head of the implant abutment retaining screw, direct threading abutment, or threaded fastener. Drive shaft 74 may be constructed of any material sufficiently strong to accomplish this function. Preferred materials for the drive shaft include heat treatable stainless steel in either alloys 440A, 440B, or 440C, although other materials may be used. The shape of the drive shaft is primarily cylindrical in shape. A broached blind hole comprises the drive shaft's shear pin engaging means 76. This shear pin engaging means is not visible in FIG. 6, but is shown in FIG. 7. The drive shaft's shear pin engaging means 76 is preferably hexagonal in cross sectional shape to correspond to the cross sectional shape of the drive shaft engaging means of the shear pin, but may be any cross sectional shape other than round. The drive shaft shear pin engaging means outside diameter 78 is substantially the same as the shear pin's drive shaft stop, which means that the drive shaft's shear pin engaging means outside diameter 78 is also substantially smaller than the crossbore of the wrench handle. This isolates the drive shaft from having any contact with the wrench handle during use and this feature contributes considerably to the invention's accurate delivery of torque, eliminating frictional forces that would add additional unwanted and unpredictable torque delivered to the drive shaft. The drive shaft's shear pin engaging means outside diameter 78 is substantially larger in diameter than the wrench handle crossbore exit 46. This allows the drive shaft to be retained within the wrench handle after the shear pin shears, preventing loss in the operating field and/or aspiration by the patient. Broach relief diameter of the drive shaft 80 allows sufficient depth of drilling of a pilot hole for the broaching operation of the drive shaft shear pin engaging means, and still retain sufficient strength of the drive shaft to function without failure, and allow clearance of the wrench handle cross-bore exit 46 such that the drive shaft has no contact whatsoever with the wrench handle. Drive shaft extension 82 is essentially cylindrical in shape and may be of varying length and diameter. Diameter of the drive shaft extension 82 must be equal to or smaller than the broach relief diameter 80 to allow passage of the drive shaft through the exit end of the cross-bore of the wrench handle 46. Drive end of the drive shaft of the invention 84 functions by engaging the screw head of the implant abutment retaining screw or direct threading abutment, or threaded fastener. The drive end of the drive shaft 84 can be of various cross sectional shapes and sizes with hex, square and Torx® being the most popular shapes.

FIG. 7 is a bird's eye or top view of the drive shaft of the invention. 86 corresponds to the drive shaft shear pin engaging means outside diameter. 88 corresponds to the broached blind hole of the drive shaft which constitutes the drive shaft shear pin engaging means. The shape of the broaching corresponds to the cross sectional shape of the shear pin's drive shaft engaging means. The cross sectional shape of the shear pin engaging means of the drive shaft 88 is preferably hexagonal in shape, but may be any cross sectional shape other than round.

FIG. 8 is a side view of an alternative embodiment of the shear pin of the invention. This embodiment essentially combines the function of the preferred embodiment of the retaining screw and the preferred embodiment of the shear pin of the invention. At first glance, it would appear that this embodiment should be the preferred embodiment of the shear pin of the invention because it combines two parts into one. However, because the shear pin is by far the one component of the invention that will be produced in the highest quantity, simplifying the manufacture of the shear pin is of highest importance. This alternative embodiment of the shear pin of the invention is substantially more difficult, time consuming and material consuming to produce than the preferred embodiment of the shear pin of the invention. It is shown here as an example of an alternative embodiment of the shear pin that achieves the same accurate delivery of torque as the preferred embodiment of the shear pin of the invention in a physically simpler, but albeit more costly manner. An alternative embodiment of the shear pin of the invention 90 is comprised of a tapered head of the shear pin 92, two flats 94 (only one is visible in FIG. 8), to allow easier insertion and removal of the shear pin into the wrench handle of the invention. Countersink 96 corresponds in shape and size to the countersink milled in the wrench handle and centers the alternative embodiment of the shear pin in the cross-bore of the wrench handle as well as provides a stop for the alternative embodiment of the shear pin of the invention. Thread relief 98 is similar to the thread relief of the preferred embodiment of the retaining screw of the invention. Left hand threads 100 that correspond to the left hand threads of the crossbore of the wrench handle. Shear groove 102 forces shear of the alternative embodiment of the shear pin of the invention in the exact same manner as the preferred embodiment of the shear pin of the invention, producing identical results as the preferred embodiment of the shear pin of the invention. Drive shaft stop 104 of the alternative embodiment of the shear pin of the invention is shaped and functions identically to the drive shaft stop of the preferred embodiment of the shear pin of the invention. Drive shaft engagement means 106 of the alternative embodiment of the shear pin of the invention is shaped and functions identically to the drive shaft engagement means of the preferred embodiment of the shear pin of the invention. This alternative embodiment of the shear pin of the invention is also constructed preferably of the same Alloy 360 brass material as the preferred embodiment of the shear pin of the invention, but may be constructed of other materials. This alternative embodiment of the shear pin of the invention functions identically in every way to the preferred embodiment of the shear pin of the invention. It is physically a simpler solution to torque delivery, but is substantially costlier to manufacture.

It is contemplated that this torque wrench can be offered as a kit with one wrench handle, one retaining screw, and a number of shear pins of all one preset torque or of various preset torques. Additionally, the kit could include either one or a plurality of drive shafts to adapt to as many implant systems or different types of threaded fasteners as possible. The wrench handles, retaining screws and drive shafts may be designed for single use (disposable) or for repeated usage. The shear pins by design are single use only. The components of the kit may be made in any size to accommodate greater loads in general orthopedic applications.

Alternative embodiments of the present invention have been described. Nevertheless, it will be understood that various modifications may be made without departing from the spirit and scope of the invention. Accordingly, it is to be understood that the invention is not to be limited by the specific illustrated embodiments but only by the scope of the appended claims.

What is claimed is:

1. A tool for tightening components of a denture, said tool comprising an elongated handle having a head portion and a bar portion, a bore through said head portion, said bore having a shaped interior and a bore exit, a shear pin comprising an elongated shaft disposed in said bore, said elongated shaft having a first end portion, an intermediate shear pin portion and a second end portion, said first end portion fixed in said shaped interior, said second end portion extending through said bore exit, a retaining means in said bore for capture of said second end portion whereby torque applied by said handle and said second end portion to a denture shears said shear pin and said second end portion remains in said bore.

2. A tool of claim 1 wherein as first opening is formed in said head portion at one end of said bore, said bore exit is formed in said head portion at the other end of said bore, said first opening being larger than said bore exit, and said shaft having a portion larger than said bore exit.

3. A tool of claim 2 wherein said bore includes an internal thread and an external thread on said shaft, said internal thread and said external thread cooperating to secure said shaft in said bore, said internal thread and external thread oriented in the opposite direction from the direction of torque whereby applying torque to said denture component will tighten said shaft in said bore.

4. A tool of claim 1 wherein said bore includes an internal thread and an external thread on said shaft, said internal thread and said external thread cooperating to secure said shaft in said bore, said internal thread and external thread oriented in the opposite direction from the direction of torque whereby applying torque to said denture component will tighten said shaft in said bore.

5. A tool of claim 1 wherein said shear pin portion and said second portion are free of contact with said bore.

6. A tool kit for tightening components of a prosthesis, said kit comprising at least one handle having a head portion and an elongated bar, said head portion having a bore therethrough, a first opening in said head portion at one end of said bore, a bore exit in said head portion at the other end of said bore, said first opening being larger than said bore exit, a plurality of shear pins each including a shaft adapted to be secured in said bore, each of said shafts having an extension for engaging a component of a prosthesis, an intermediate shear pin portion and a first end portion, said first end portion of each of said plurality of shafts adapted to be rotationally fixed in said bore, each of said extensions of said plurality of shafts and said shear pin portions of each of said plurality of shafts adapted to be free of contact with said bore, each of said extensions of said plurality of said shafts adapted to be retained by said bore exit whereby several tools may be assembled sequentially and said extensions will not separate from said handle, said head portion and said plurality of shear pins each having cooperating screw threads whereby tightening of a prosthesis tightens said cooperating screw threads.

7. A tool kit of claim 6 wherein said kit includes a plurality of different shafts, said shafts each having a different sized extension for engaging different sized prosthesis components.

8. A tool kit of claim 6 wherein each of said plurality of said shafts reach having a shear pin portion with a different shear strength for applying different amounts of torque to different prosthesis.

9. A tool kit of claim 6 wherein each of said plurality of shear pin portions will shear within approximately ±0.3 Ncm of each other.

* * * * *